US00PP23649P3

(12) United States Plant Patent
Shefelbine

(10) Patent No.: US PP23,649 P3
(45) Date of Patent: Jun. 4, 2013

(54) APPLE TREE, 'DS 3'

(50) Latin Name: *Malus Domestica*
Varietal Denomination: DS 3

(76) Inventor: Doug Shefelbine, Holman, WI (US)

( * ) Notice: Subject to any disclaimer, the term of this patent is extended or adjusted under 35 U.S.C. 154(b) by 160 days.

(21) Appl. No.: 13/135,511

(22) Filed: Jul. 7, 2011

(65) Prior Publication Data

US 2013/0014299 P1 Jan. 10, 2013

(51) Int. Cl.
*A01H 5/00* (2006.01)

(52) U.S. Cl.
USPC ..... Plt./161

(58) Field of Classification Search ..... Plt./161
See application file for complete search history.

*Primary Examiner* — Annette Para
(74) *Attorney, Agent, or Firm* — Paine Hamblen, LLP

(57) ABSTRACT

A new and distinct variety of apple tree is described and which is somewhat similar in its overall characteristics to that of the 'Honeycrisp' apple tree (U.S. Plant Pat. No. 7,197) but which is distinguishable therefrom by producing fruit which are ripe for harvesting and shipment about 10 days later then the 'Honeycrisp' apple tree when grown under the prevailing ecological conditions which occur near Ephrata, Wash.

4 Drawing Sheets

Latin name: *Malus Domestica.*
Varietal name: 'DS 3'.

BACKGROUND OF THE NEW VARIETY

The present invention relates to a new, novel, and distinct variety of apple tree '*Malus Domestica*' and which has been denominated varietally as 'DS 3' and more specifically to a novel apple tree which produces fruit which are ripe for harvesting and shipment at least about 10 days later than the variety it is most similar to, that being, the 'Honeycrisp' apple tree (U.S. Plant Pat. No. 7,197) when it is grown under the same cultural conditions and at the same geographical location.

ORIGIN AND ASEXUAL REPRODUCTION

It has long been recognized that an important factor contributing to the success of any new variety of apple tree bearing fruit for the fresh market, is its relative date of harvesting in comparison to other varieties bearing similar fruit, in the same season. Further, another significant factor affecting the commercial viability of a new variety of apple tree relates to the appearance of the fruit it produces, as well as its fruit size, and an attractive coloration.

The new variety of apple tree, as described herein, 'DS 3' was derived by the following methodology. Seeds from an open pollinated 'Honeycrisp' apple tree (U.S. Plant Pat. No. 7,197) were collected during the 1990 growing season. These same seeds were then planted in 1991 at an orchard which I control and which is located near North 6485 Shefelbine Rd., Holman, Wis. This orchard is located in USDA Hardiness Zone 4A. The seeds which were planted in 1990, and the trees which grew from these seeds, were cared for and observed, and the new variety 'DS 3' was selected from among the surviving seedlings during the 2002 growing season. Propagation wood was then removed from this promising seedling and was then grafted into EMLA 26 rootstock which was then planted, and growing in a nursery which operates near Ephrata, Wash. The test orchard in Ephrata Wash. is located in USDA hardiness zone 6A. Fruit generated by these second generation trees were observed during the 2009 and 2010 growing seasons. It has been determined that the fruit produced by these trees and the other characteristics observed are the same as that seen in the original seedling that was first identified during the 2002 growing season.

SUMMARY OF THE VARIETY

The 'DS 3' apple tree is characterized as to novelty by producing an attractively colored fruit which is ripe for harvesting and shipment about September 19$^{th}$ under the ecological conditions prevailing in Ephrata, Wash. This date of harvesting is 10 days later than the closest known variety, that being, the 'Honeycrisp' apple tree (U.S. Plant Pat. No. 7,197) from which it was derived as a chance seedling. The new variety of apple tree produces a fruit which has a skin appearance which appears glaborous, and which further has a distinctive stripe as opposed to the blotchy exterior appearance of the fruit produced by the aforementioned 'Honeycrisp' apple tree. Further, the new variety of apple tree produces fruit which are one to two sizes larger than that produced by comparatively cropped trees 'Honeycrisp' apple trees when grown under the same ecological conditions in Ephrata, Wash. In addition to the foregoing, the fruit produced by the present variety exhibits a higher acidity and lower pH levels than that fruit produced by the 'Honeycrisp' apple trees growing in the same geographical area.

BRIEF DESCRIPTION OF THE DRAWINGS

The accompanying drawings are color photographs of the present variety.

Figure 1:
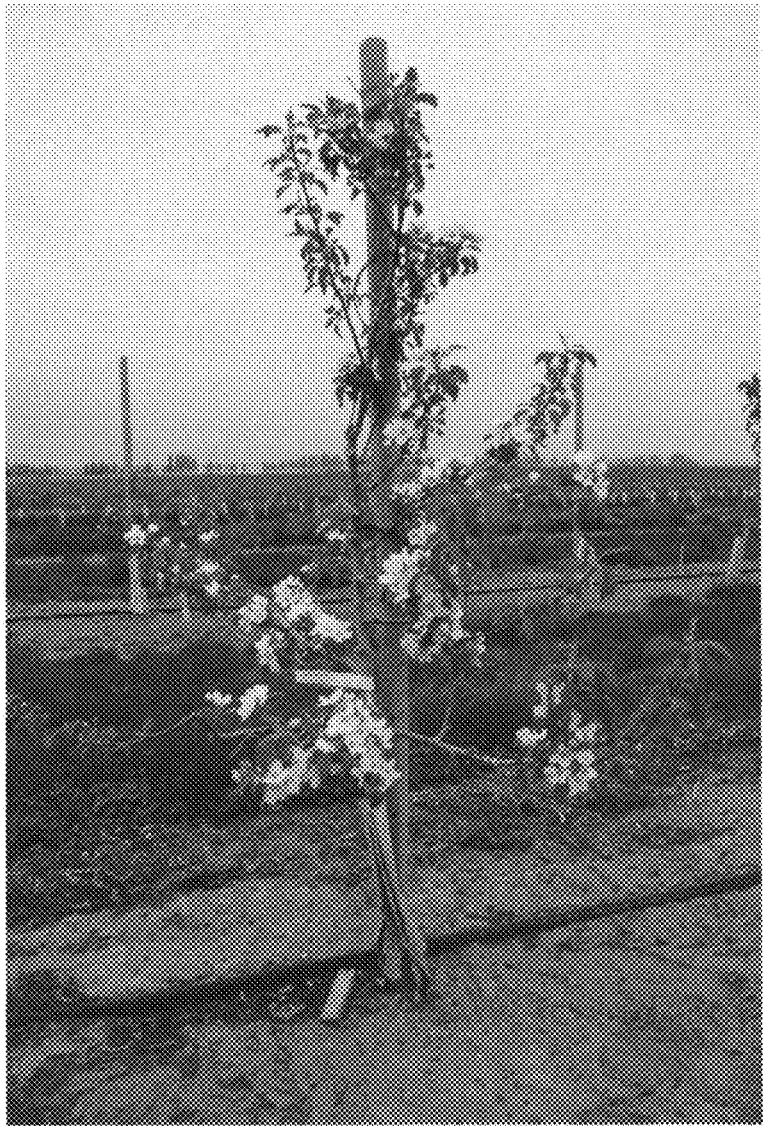
FIG. 1 depicts a second generation tree of the present variety at full bloom.
Figure 2:
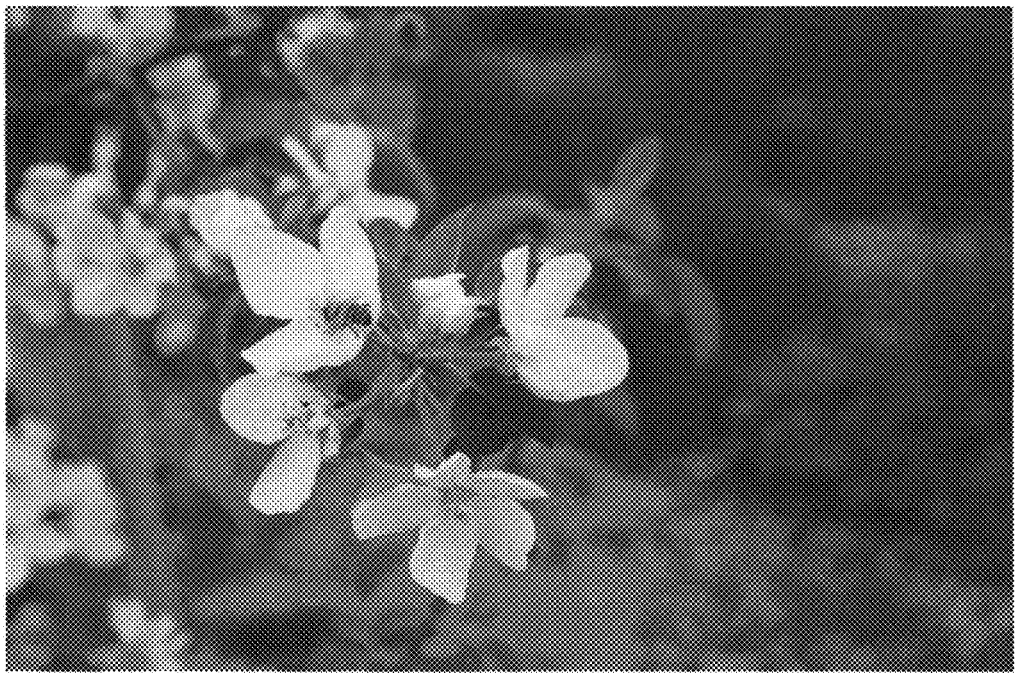
FIG. 2 depicts the blossom characteristics of a second generation tree of the present variety.
Figure 3:
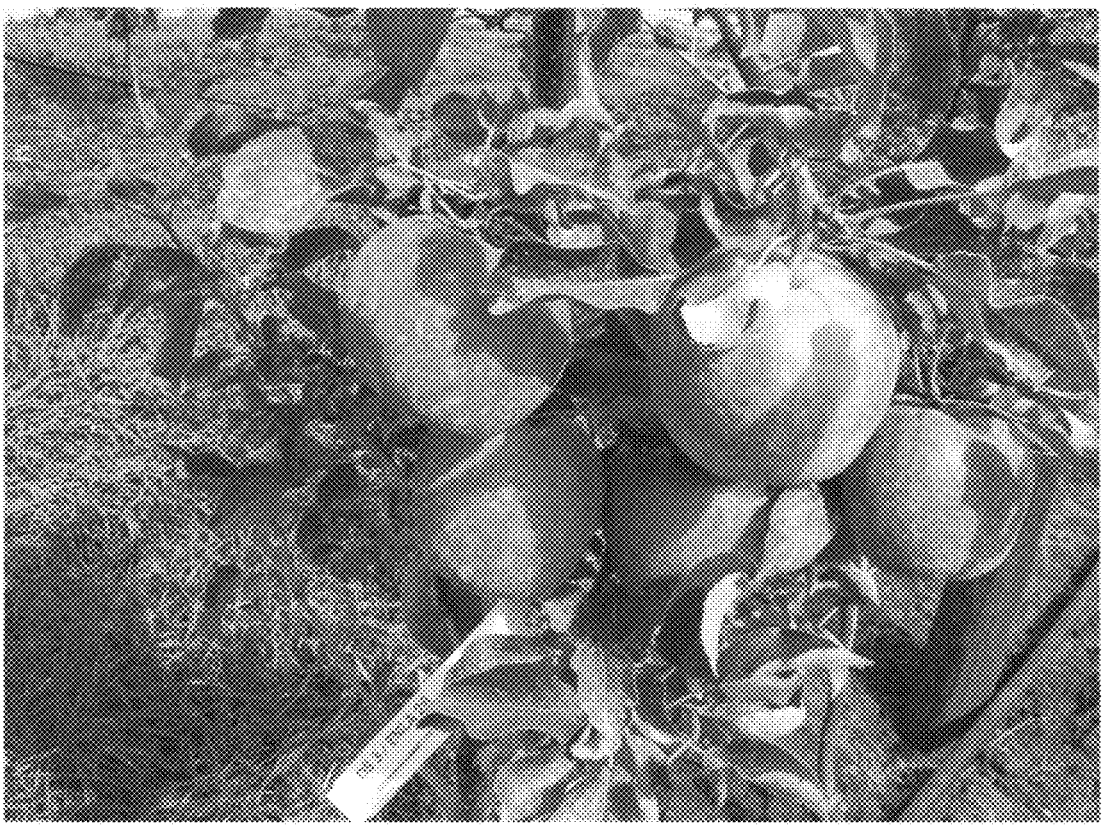
FIG. 3 depicts the fruiting characteristic of a second generation tree of the new variety at full harvest maturity.
Figure 4:
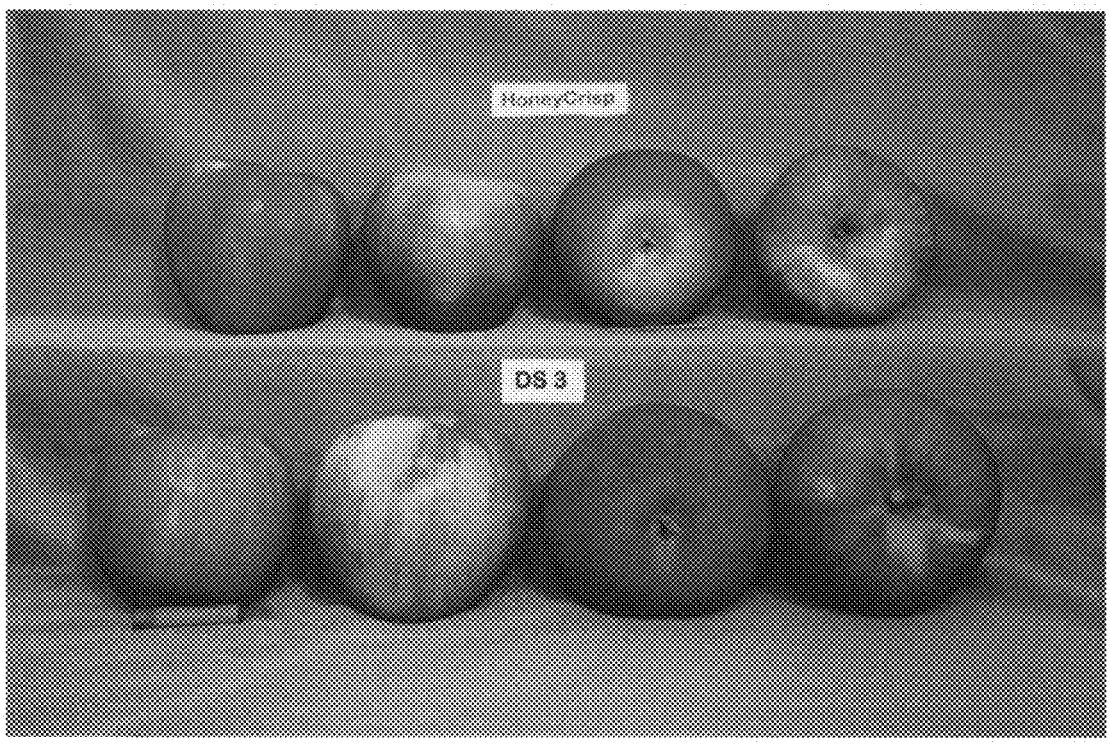
FIG. 4 shows the fruit of the present variety 'DS 3' as compared to the fruit of the 'Honeycrisp' apple tree (U.S. Plant Pat. No. 7,197) at full harvest maturity. The fruit shown in this view were harvested from trees grown in the same geographical location.

The colors in the enclosed photographs are as nearly true as is reasonably possible in color photographs of this type. However, due to chemical development, processing and printing, the leaves and fruit depicted in these photographs may or may not be accurate when compared to the actual botanical specimens. For this reason, future color references should be made to the color plates (Royal Horticultural Society of Great Britain) and other common color descriptions as provided hereinafter.

NOT A COMMERCIAL WARRANTY

The following detailed description has been prepared to solely comply with the provisions of 35 U.S.C. §112, and does not constitute a commercial warranty, (either expressed or implied), that the present variety will in the future display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological and botanical details of this new and distinct variety of apple tree, the following has been observed during the 2010 growing season under the ecological conditions which prevailed in a test orchard which is located near Ephrata, Wash. All major color code designations are by reference to The R.H.S. Colour Chart, 3rd Edition provided by The Royal Horticultural Society of Great Britain.

TREE

Size:
*Generally*.—Considered average for the species.
Tree height: About 7.5 feet.
Crown width: About 5.5 feet.
Tree form: The present tree is grown on a central leader type arrangement.
Spur development: The present variety produces moderately heavy spurs and is considered precocious.
Tree vigor: Considered moderate for the species.
Overall shape: Considered upright to upright spreading.
Hardiness: Considered hardy in USDA zone 6a.
Fruit productivity: Generally considered moderate for the species.

TRUNK

Size: About 4.6 cm. in diameter when measured at a height of about 20 cm. above the graft union.
Bark texture: Considered slightly rough and having a webbed pattern.
Bark color: Grey-Brown (RHS Group 199A).
Bark lenticels:
*Generally*.—Present, and moderate in number, averaging about 15 per 9 square cm. region.
Bark lenticels:
*Shape*.—Elongated oval.
Bark lenticels:
*Width*.—About 1 mm.
Bark lenticels:
*Length*.—About 3.8 mm. to about 7.2 mm.
Bark lenticels:
*Color*.—Orange-White (RHS Group 159A).

BRANCHES

First year branches:
*Diameter*.—About 5 mm. to about 5.8 mm. when measured at the mid-point of growth.
First year branches:
*Length*.—About 30.5 mm. to about 45.5 mm.
Branch bark color: Grey-Red (RHS 178A).
Branch lenticels:
*Numbers*.—Numerous and typically having about 19 lenticels per running cm.
Branch lenticels:
*Shape*.—Oval and having a size of about 0.6 mm. in length; and about 0.3 mm. in width.
Branch lenticels:
*Color*.—White (RHS 155D).
Branch pubescence: Present and considered moderate, in abundance.
Branch pubescence:
*Color*.—White. This color is not distinctive of the present variety, however.
Internodes:
*Length*.—About 2.5 to 3.9 cm.
2 year old fruiting branches:
*Diameter*.—About 8.6 mm. to about 9.7 mm.
2 year old wood:
*Spur development*.—Considered moderate in density and elongated.
2 year old wood:
*Spur length*.—About 20.1 mm. to about 24.4 mm.
2 year old wood:
*Bud length*.—About 8.2 to about 9.6 mm.
2 year old wood:
*Bud shape*.—Cone-like.
2 year old wood:
*Bud color*.—Grey-Brown (RHS N199B).
2 year old wood:
*Lenticels*.—Generally speaking the lenticels are numerous, and average about 7 per square cm.
2 year old wood:
*Lenticels shape*.—Oval and being about 0.9 mm. in width and about 1.6 mm. in length.
2 year old wood:
*Lenticel color*.—White (RHS N155D).
2 year old wood:
*Bark color*.—Grey-Orange (RHS 165A).
Scaffold branches:
*Size*.—About 16.8 mm. to about 22.7 mm. in diameter when this dimension is taken at a location about 10 cm. from the trunk.
Scaffold branches:
*Crotch angle*.—Considered moderate to flat, ranging from about 80 to 90 degrees from the vertical axis, as it is trained.
Scaffold branches:
*Color*.—Grey-Brown (RHS N199C).

Scaffold branches:
*Lenticels*.—Generally considered moderate in number and having usually about 5 lenticels per square cm.
Lenticels:
*Shape*.—Considered elongated and slender.
Lenticels:
*Length*.—About 2.3 to about 3.3 mm.
Lenticels:
*Color*.—Grey-White (RHS 156D).

LEAVES

Leaf shape: Generally considered broadly acute and upwardly lifted.
Leaf texture: The dorsal surface appears leathery, and slightly undulating. The ventral surface is considered glabrous.
Leaf sheen: The dorsal surface has a high sheen.
Leaf pubescence: Present. On the dorsal surface, the pubescence is considered to be sparse and very fine. The ventral surface, on the other hand, is substantially completely covered with pubescence.
Pubescence:
*Color*.—For both the ventral and dorsal surfaces, the pubescence has a grey-yellow color (RHS 161A).
Leaf length: About 76.1 mm. to about 107.0 mm.
Leaf width: Ranging from about 50.1 mm. to about 68.9 mm.
Leaf marginal edge: Considered mostly serrate. The marginal edge also displays some bi-serrate regions.
Leaf tip:
*Shape*.—Acuminate.
Leaf base:
*Shape*.—Rounded.
Leaf stipules:
*Generally*.—Present and considered prominent.
Leaf stipules:
*Numbers*.—Typically 2 stipules appear per petiole.
Leaf stipules:
*Length*.—About 10.6 mm. to about 18.8 mm.
Leaf stipules:
*Width*.—About 1.7 mm. to about 3.7 mm.
Leaf stipules:
*Color*.—The dorsal surface has a yellow-green color (RHS 147A). The ventral surface has a yellow-green color (RHS 147C).
Leaf stipules:
*Pubescence*.—The leaf stipule pubescence is usually only present on the ventral surface. It is considered fine and covers the entire surface.
Leaf stipule pubescence:
*Color*.—Grey-Yellow (RHS 161A).
Leaf blade color:
*Dorsal surface*.—Yellow-Green (RHS 147A).
Leaf blade color:
*Ventral surface*.—Yellow-Green (RHS 147B).
Mid-vein:
*Shape*.—Considered prominent, and having a considerable amount of fine pubescence under the surface of the vein.
Mid-vein:
*Width*.—When measured at mid-blade about 1 mm. to about 1.9 mm.
Mid-vein:
*Color*.—The dorsal surface has a yellow-green color (RHS 145C).
Mid-vein:
*Pubescence color*.—Grey-Yellow (RHS 161A).
Petiole:
*Length*.—About 25.3 to about 31.7 mm.
Petiole:
*Diameter*.—When measured at the mid-point, it is about 1.5 mm to about 2.6 mm.
Petiole:
*Color*.—Generally, Yellow-Green (RHS 145A). Further, at the basal end thereof, the color is grey-red (RHS 178A).
Petiole:
*Pubescence quantity*.—Considered abundant, and fine over the length and circumference of the petiole.
Petiole pubescence color: Grey-White (RHS 156A).

FLOWERS

Date of full bloom: In 2010 full bloom occurred on April 29$^{th}$.
Number of blossoms per bud: Usually about 3 to 6.
Flower size:
*Generally*.—Considered medium, to medium large for the species. When fully expanded, the flower has a diameter from about 50 to about 57 mm.
Flower petal:
*Length*.—About 22 to about 26 mm.
Flower petal:
*Width*.—About 18 to about 21 mm.
Flower petal color: White (RHS N155B), and having some grey-purple regions (RHS 186C).
Petal vein color: Grey-Purple (RHS 186B).
Flower stamens:
*Numbers*.—19-20.
Flower filaments:
*Length*.—5 to about 10 mm.
Flower filament color: White (RHS 155A).
Anthers:
*Shape*.—Kidney like, and having a length of about 2.6 mm; and a width of about 2.3 mm.
Anthers:
*Color*.—Grey-Yellow (RHS 162B).
Pistil:
*Length*.—About 11.2 to about 12.7 mm.
Pistil:
*Color*.—Yellow-Green (RHS 145C).
Stigma:
*Shape*.—Club-like.
Sigma:
*Color*.—Yellow-Green (RHS 152D).
Sepals:
*Numbers*.—Typically 5 sepals are found per blossom. They are usually curled back towards the peduncle.
Sepals:
*Shape*.—Generally considered deltoid.
Sepals:
*Tip shape*.—Acuminate.
Sepals:
*Base shape*.—Truncate.
Sepals:
*Length*.—About 9.5 mm.
Sepals:
*Width*.—About 4.7 mm.
Sepals:
*Pubescence quantity*.—Generally it is abundant, and present on both the upper and lower surfaces. The pubescence is white. This particular color is not distinctive of the variety, however.

Sepal:

*Color*.—Yellow-Green (RHS 144A). The sepal tips are highlighted with a grey-brown color (RHS N199C).

Peduncle:

*Length*.—About 21 to about 24 mm.

Peduncle:

*Color*.—Yellow-Green (RHS 144A), and occasionally having highlights of grey-brown (RHS N199C).

Peduncle:

*Downiness*.—A considerable amount of white downiness is present over the entire surface. This particular color is not distinctive of the new variety, however.

FRUIT

Maturity when described:

*Generally*.—The fruit produced by the present variety of apple tree is described, hereinafter, as it would be found at full commercial maturity. In this regard, the fruit of the present variety was ripe for commercial harvesting and shipment under the ecological conditions prevailing near Ephrata, Wash. on Sep. 19, 2010. In relative comparison to the 'Honeycrisp' apple tree which is grown at the same geographical location and under the same cultural conditions the fruit produced by the 'Honeycrisp' apple tree (U.S. Plant Pat. No. 7,197) was ripe for harvesting and shipment about 10 days earlier on Sep. 9, 2010.

Fruit form: Considered round-conical. The equatorial outline, or shape is angular and the fruit appears lopsided.

Fruit size: Considered large for the species at normal crop loads.

Fruit diameter: About 88.6 mm.

Axial diameter: About 77.4 mm.

Fruit stem:

*Generally*.—Considered medium thick, with an average thickness of 3 mm. when measured at the midpoint.

Fruit stem:

*Length*.—Considered medium short. About 16.8 mm.

Stem cavity:

*Width*.—About 35.5 to about 42.3 mm.

Stem cavity:

*Depth*.—About 15.4 to about 21.8 mm.

Stem cavity:

*Shape*.—Abrupt.

Stem cavity:

*Ribbing*.—Not apparent.

Basin cavity:

*Width*.—About 30.6 to about 38.1 mm.

Basin cavity:

*Depth*.—About 10.6 to about 14.9 mm.

Basin cavity:

*Shape*.—Considered abrupt. The basin cavity is not ribbed.

Eye:

*Shape*.—Erect with reflexed tips.

Sepal color is green (RHS N138D).

Sepals:

*Surface texture*.—Downy. The downy color is white (RHS 155C).

Fruit skin:

*Surface texture*.—Considered moderately tough, and generally glabrous and having a moderate amount of bloom present.

Fruit skin:

*Thickness*.—Considered medium thick for the species.

Fruit skin appearance:

*Generally*.—A stripe covers 80 to about 100 percent of the fruit skin surface.

Fruit skin color: The stripe over-color appearing on the fruit skin is red (RHS 53A). The undercolor of the fruit skin is grey-yellow (RHS 162D).

Fruit skin lenticels:

*Generally*.—Present, however, they are small, smooth and are generally uniformly distributed.

Lenticels color: White (RHS 155D).

Lenticels:

*Size*.—Generally — Round, and about 0.2 to about 0.6 mm. in diameter.

Fruit core position: Considered distant.

Fruit core line position: Considered medium.

Fruit core diameter: About 38.1 to about 52.1 mm.

Fruit core length: About 29.4 to about 31.4 mm.

Fruit cell:

*Numbers*.—5 per fruit are found.

Fruit cell:

*Form*.—Not tufted.

Fruit cell shape: Elliptical.

Fruit cell length: About 17.9 mm.

Fruit cell width: About 12 mm.

Fruit cell depth: About 6.2 mm.

Tube:

*Shape*.—Cone shaped.

Stamen position: Generally considered basal.

Axis:

*Orientation*.—Axial and open.

Seeds: 1 or 2. Generally speaking, mostly 2.

Seeds:

*Shape*.—Acute.

Seeds:

*Length*.—About 7.1 to about 8.5 mm.

*Seed width*.—About 4.2 to about 5.3 mm.

Seed color: Grey-Brown (RHS N199C).

Flesh:

*Firmness*.—The flesh is considered firm, crisp, melting and juicy.

Flesh color: Yellow (RHS 13D). A lighter color bleeding into the flesh is typically seen. The bleeding color is red (RHS 53A). The flesh of the present variety will brown slightly following cutting.

Aroma:

*Generally*.—Mild and apple like.

Date of maturity for harvesting and shipment: Sep. 19, 2010 under the ecological and cultural conditions prevailing in the orchard identified above in Ephrata, Wash. This date of harvesting is 10 days later than the 'Honeycrisp' apple tree which are grown under similar cultural conditions in Ephrata, Wash.

Fruit pressure: About 13.8 pounds. This is similar to that produced by the 'Honeycrisp' apple tree at its date of maturity.

Brix: About 13.7. This brix is slightly lower than the average brix of the 'Honeycrisp' apple tree, that being about 13.8.

pH: The new variety has a flesh pH of about 3.18. In relative comparison to the fruit produced by the 'Honeycrisp' apple tree, this pH is somewhat higher than that of the 'Honeycrisp' apple tree which is 3.35.

Soluble solids: The present variety has a soluble solid of about 0.89 grams per 100 milliliters. In comparison, the fruit produced by the 'Honeycrisp' apple tree has a soluble solids reading of about 0.66 grams per 100 milliliters.

Storage quality: Considered good. The present variety has been stored up to 4 months with no deleterious effects noted.

Pollination: The present variety may be pollinated by any diploid apple having approximately the same blooming season.

Fruit use: Considered to be a fresh dessert apple.

Disease and insect resistance: The present variety is considered to be susceptible to all insects and diseases found in the region of Central Washington state.

Although the new variety of apple tree possesses the described characteristics when grown under the ecological conditions prevailing in Ephrata, Wash., in the south central part of Washington state, it should be understood that variations of the usual magnitude and characteristics incident to changes in growing conditions, fertilization, pruning and pest control as well as horticultural management practices are to be expected.

Having thus described and illustrated my new variety of apple tree, what I claim is new, and desire to secure by plant Letters Patent is:

1. A new and distinct variety of apple tree '*Malus domestica*' as substantially illustrated and described, which is characterized principally as to novelty by bearing an attractively colored apple which is ripe for harvesting and shipment about September $19^{th}$ under the ecological conditions prevailing near Ephrata, Wash.

* * * * *